US008332240B1

(12) United States Patent
Garver et al.

(10) Patent No.: US 8,332,240 B1
(45) Date of Patent: Dec. 11, 2012

(54) METHOD AND SYSTEM FOR TRACKING AND MONITORING VACCINE AND PHARMACEUTICAL INFORMATION

(75) Inventors: Michael K Garver, Great Falls, MT (US); Burl Duane Williams, Bozeman, MT (US); Darcy Zanto, Highwood, MT (US)

(73) Assignee: VEMR, Inc., Great Falls, MT (US)

( * ) Notice: Subject to any disclaimer, the term of this patent is extended or adjusted under 35 U.S.C. 154(b) by 468 days.

(21) Appl. No.: 12/614,579

(22) Filed: Nov. 9, 2009

Related U.S. Application Data

(60) Provisional application No. 61/113,313, filed on Nov. 11, 2008.

(51) Int. Cl.
*G06Q 50/00* (2012.01)
(52) U.S. Cl. ................................. 705/3; 705/2
(58) Field of Classification Search .................. 705/2, 3
See application file for complete search history.

(56) References Cited

U.S. PATENT DOCUMENTS

| | | | |
|---|---|---|---|
| 5,667,303 A | 9/1997 | Arens et al. | |
| 6,021,392 A | 2/2000 | Lester et al. | |
| 6,611,806 B1 | 8/2003 | Harvey | |
| 7,102,526 B2 | 9/2006 | Zweig | |
| 7,182,259 B2 | 2/2007 | Lubow et al. | |
| 7,261,235 B2 | 8/2007 | Barenburg et al. | |
| 7,370,797 B1 | 5/2008 | Sullivan et al. | |
| 2002/0072991 A1 | 6/2002 | Kane | |
| 2003/0055685 A1 | 3/2003 | Cobb et al. | |
| 2003/0160698 A1 | 8/2003 | Andreasson et al. | |
| 2004/0243620 A1* | 12/2004 | Carter et al. ................... | 707/102 |
| 2005/0283259 A1 | 12/2005 | Wolpow | |
| 2006/0015536 A1 | 1/2006 | Buchanan et al. | |
| 2006/0106645 A1 | 5/2006 | Bergelson et al. | |
| 2007/0043469 A1* | 2/2007 | Draper ........................... | 700/231 |
| 2007/0150312 A1 | 6/2007 | Schmidt | |

FOREIGN PATENT DOCUMENTS

WO WO 03/087996 A2 10/2003

* cited by examiner

*Primary Examiner* — Lena Najarian
(74) *Attorney, Agent, or Firm* — Christine McLeod; Beusse Wolter Sanks Mora & Maire PA

(57) ABSTRACT

An improved system, method and computer-readable instructions for tracking and monitoring vaccine and pharmaceutical information including data storage and environment sensing is provided. The improved method includes the steps of reading a tag associated with the vaccine, where the tag includes first information about the product and second information about the product recorded by an environmental sensor. The improved method further includes the step of determining the safety and efficacy of the product based on the readings from the tag, by comparing the first information including an expiration date with a current date to determine whether the vaccine has expired and by comparing the second information including a range of environments to a predetermined acceptable threshold range of environments indicating whether the product has exceeded the threshold.

26 Claims, 4 Drawing Sheets

METHOD AND SYSTEM FOR TRACKING AND MONITORING VACCINE AND PHARMACEUTICAL INFORMATION

This application claims priority to provisional application Ser. No. 61/113,313 filed Nov. 11, 2008, incorporated herein by reference.

BACKGROUND OF THE INVENTION

1. Field of the Invention

This invention relates to tracking and monitoring information, and specifically to an improved system, method, and computer-readable instructions for tracking and monitoring vaccine and pharmaceutical information including data storage and environment sensing.

2. Discussion of the Background

It is known that vaccines are sensitive to both excessive heat and excessive cold. Therefore, it is important that vaccines and other drugs be transported and stored correctly. Careful attention is needed in handling practices from the source to the end-user at the health facility. This can only be achieved by appropriate environmental monitoring. The CDC recommends that information regarding the storage temperatures is to be recorded at least twice a day in a temperature log. However, without continuous monitoring, there remains a possibility that the temperature exceeded a specific threshold for a vaccine/drug.

Moreover, all vaccines and diluents have expiration dates. Expiration dates vary by the type of vaccine or diluent, and by the lot number. Failure to monitor the elapsed time may also lead to expiry of vaccines during storage. The expiration date printed on each vial or box assumes the vaccine has been properly transported and stored at all times and that it has not become contaminated.

During transport, the temperature of vaccines may be monitored by cold chain monitors (CCMs). There are generally three types: those that indicate whether packages have reached temperatures that are too warm, those that indicate whether packages have reached temperatures that are too cold, and those that continuously record the temperature. These types of monitors are designed to be irreversible indicators of inappropriate temperatures. CCMs are not a substitute for twice-a-day temperature reading and recording. Every vaccine storage unit compartment should have its own certified calibrated thermometer for this purpose.

Digital data loggers (DDLs) are miniature, battery-operated, electronic devices that may be programmed to record temperatures at intervals throughout the day. Data loggers are capable of recording hundreds or even thousands of individual temperature readings. Digital data loggers used in vaccine transport have external lights that alert the user to out-of-range temperature events-a green light indicating the cold chain was properly maintained and a red light indicating inappropriate temperature exposure occurred. If a red light is displayed, the vaccine shipment must await approval for use and the device must be sent back to the manufacturer to interpret the temperature data. A special software program must be used to download the temperature data to a computer. Digital data loggers may also be used in vaccine storage units.

However, even with the use of CCMs and DDLs with vaccine shipments and storage units, there is still a possibility that an individual vial or container may have been mistakenly left out of the storage unit for a longer period of time than is acceptable, resulting in damage to the vaccine/drug. Therefore, there is a need in the art for individual monitoring of each vial or container to ensure proper handling and storage. There is also a need in the art for a simple means to retrieve and store this data.

Inventory accounting is also an important factor in vaccine quality management. Proper management includes knowing quantities received, current stock, expiration dates, excess supplies, and inventory needed to be reordered. Stock records may be kept in either computerized or written formats. Some state or local health department immunization programs have developed tally sheets or other vaccine inventory protocols and procedures for vaccine providers. Therefore, inventory management is often a time consuming process. There is a need in the art for a more simplified procedure for tracking inventory.

For example, if a patient qualifies for a government funded vaccine program called Vaccines for Children (VFC), the nurse has to manually register the immunization on a tally sheet. The tally sheets for VFC keep track (for that program) of: vaccines on hand, number of each type of vaccine given, vaccines received during the month, vaccines wasted and number of vaccines left at the end of the month. During certain months, the VFC program also requires (in addition to the normal tally sheet) that for each pt, the nurse manually writes down: every pt that received a VFC vaccine, the patients (pt) date of birth (DOB), what the pt received, and which dose. Also once a year the VFC program "audits" the private office and the nurse is required to present at least 50 immunization records of pts that have the DOBs between the requested dates. During these 'audits' the VFC program checks the refrigerator and freezer temperature logs for the entire year. The requirement is that the facility carrying VFC vaccine must check their storage temperatures twice a day, for every day that the practice is open and record this information.

When vaccines are administered, most vaccines are also charted in an electronic medical record (EMR) for the patient. The fact that nurses are using computers to chart these injections minimally increases the speed and accuracy. For example, in current systems, nurses can click on the type of vaccine, but then have to manually enter: lot number, expiration date, route of administration, site, manufacturer and when it was given. There is a need in the art for a more simplified process of recording this information.

Another chart that it required is the Vaccine Information Sheet date (VIS). This is charted to indicate that the parent was told about the VIS. It is the parents' choice to take or refuse the VIS, but the nurse must chart that they have the sheet available for each and every vaccine that is carried in the office.

In addition to computer and paper charting, nurses are required to keep current on all state and federal requirements and standards for immunization schedules, ensuring that all pts are kept up-to-date on all their immunizations.

Once the nurse has ensured that the patient needs vaccines, charts the vaccines in all the appropriate places and gives the vaccines, governing agency request that you share that information with them, each and every time.

The City and County Health Department (CCHD) is one such governing agency. After every vaccine is given, the CCHD requests that the private practice send them: the pts name, pts DOB and what was administered and on what date. The CCHD, in turn, enters this into their database so that healthcare professionals throughout the state, can access that pt's immunization records.

With all the charting, inventory, temperature records, schedules, sharing of information and everything else required to give a patient an immunization and record it, there are obviously multiple opportunities for errors and wasted time.

Accordingly, there is a need in the art for a system that will reduce the time in charting and improve accuracy. There is also a need for a system that assists in inventory and tracking of vaccine and pharmaceutical information.

A number of patents exist that describe various types of tracking and inventory methods, such as U.S. Pat. Nos. 7,370,797, 7,261,235, US20070150312A1, 7,182,259, 7,102,526, US20060106645A1, US20060015536A1, US20050283259A1, US20030160698A1, 6,611,806, US20030055685A1, US20020072991A1, 6,021,392, 5,667,303, and international application No. WO03087996A2 all incorporated herein by reference. No admission is made that any or all of these references are prior art and indeed, it is contemplated that they may not be available as prior art when interpreting 35 U.S.C. 102 in consideration of the claims of the present application.

SUMMARY OF THE INVENTION

The present invention solves the needs in the art by providing a system and method for tracking and monitoring vaccine and pharmaceutical information that includes data storage and environment sensors on the products themselves wherein the data is easily transmitted to remote devices. Preferably, the method and system uses MEMS-enabled tags (e.g., a central unit that processes data, a microprocessor and several components that interact with the outside such as microsensors) to provide digital data storage on the tag, a communication interface (e.g., communication layer comprised of a microcontroller, RF transceiver and integrated antenna), and environment monitoring (e.g., temperature, radiation, humidity, time, etc). Preferably, such a device is capable of providing data storage, wireless communication, sensing/actuation, and event capture where the event may be a temperature or moisture alarm, etc., and data transfer. In one embodiment, the invention comprises An embodiment of the invention comprises a method for determining and tracking the safety and efficacy of a vaccine or pharmaceutical product having a tag with at least one environmental sensor and communications electronics associated therewith comprising: (a) reading a tag associated with a vaccine or pharmaceutical product received by a recipient associated with administering or disbursing the product, wherein the tag includes first information about the product, and wherein the tag further includes second information about the product recorded by an environmental sensor of the tag; (b) determining the safety and efficacy of the product based on the readings from the tag by: (ii) comparing the first information read from the tag including an expiration date with a current date to determine whether the vaccine has reached the expiration date indicating the product is expired; (i) comparing the second information read from the tag including a range of environments read from the environmental sensor prior to receipt to a predetermined acceptable threshold range of environments for the product indicating whether the product has exceeded the threshold; (c) outputting information regarding the determination of safety and efficacy wherein if either determination indicates that the product is expired or the product has exceeded the environment threshold, designating that the product is unsafe and should not be administered.

In further embodiments, the environmental sensor is activated when the product is packaged at the original place of packaging and wherein the environment sensor monitors one or more of temperature, humidity, moisture content, radiation, vibration, and light exposure. Moreover, the first information about the product comprises product information for identifying the product and its place of manufacture capable of being used for inventory and tracking purposes. The steps (a) though (c) may be repeated at predetermined intervals, including one or more of (1) prior to administering the product, (2) after a designated time period has elapsed, (3) after a change in environment that may have an effect on temperature, (4) after moving the product to another location, (5) after a power interruption at a facility where the product is located, and (6) after receiving instructions from a third party.

In further embodiments, sensors on the tag may indicate elapsed time so that the expiration can be readily determined. Embodiments also provide for writing product information to the tag by the manufacturer, packager, or recipient. Moreover, the method may include populating a database with information read from the tag by the recipient to provide for further processing of the information including one or more of updating inventory, ordering refills, verifying patient vaccine schedules, and checking recalls. It also may include communicating at least part of the information read from the tag to a central repository for remote access or processing of the information including one or more of monitoring, agency compliance, and patient accessible records.

In an embodiment, the tag comprises wireless automatic identification technology comprising one or more of a passive device, a semi-passive device, an active device, a read only device, a read/write capable device, an optically readable device, a radio frequency identification (RFID) device, and a micro electromechanical system (MEMS) device. Also, the tag may comprise a MEMS-enabled tag wherein at least one sensor is a temperature sensor. The reader may be mounted in a location proximate a storage location for the product such that the reader may periodically read the tags automatically.

A computer processor may be in communication with the reader and is adapted to receive information from the reader and transmit information to the reader. The tag may comprise a bar code device combined with an RFID device.

The invention also entails a system for determining and tracking the safety and efficacy of a vaccine or pharmaceutical product having a tag with at least one environmental sensor and communications electronics associated therewith comprising: at least one reader for reading the tag associated with the vaccine or pharmaceutical product; a computer processor in communication with the at least one reader for receiving information from the reader; the processor configured to (a) read a tag associated with a vaccine or pharmaceutical product received by a recipient associated with administering or disbursing the product, wherein the tag includes first information about the product, and wherein the tag further includes second information about the product recorded by an environmental sensor of the tag; (b) determine the safety and efficacy of the product based on the readings from the tag by: (ii) comparing the first information read from the tag including an expiration date with a current date to determine whether the vaccine has reached the expiration date indicating the product is expired; (i) comparing the second information read from the tag including a range of environments read from the environmental sensor prior to receipt to a predetermined acceptable threshold range of environments for the product indicating whether the product has exceeded the threshold; (c) output information regarding the determination of safety and efficacy wherein if either determination indicates that the product is expired or the product has exceeded the environment threshold, designating that the product is unsafe and should not be administered.

Preferably, the environmental sensor is activated when the product is packaged at the original place of packaging and wherein the environment sensor monitors one or more of temperature, humidity, moisture content, radiation, vibration, and light exposure. The first information about the product may include product information for identifying the product and its place of manufacture capable of being used for inventory and tracking purposes.

In certain embodiments, the processor is configured to repeat steps (a) though (c) at predetermined intervals, including one or more of (1) prior to administering the product, (2) after a designated time period has elapsed, (3) after a change in environment that may have an effect on temperature, (4) after moving the product to another location, (5) after a power interruption at a facility where the product is located, (6) after receiving instructions from a third party, (7) periodically throughout the day and record the temperature reading in a temperature log.

The system may include sensors on the tag indicating elapsed time so that the expiration can be readily determined. Also, product information may be written to the tag by the manufacturer, packager, or recipient.

A database may be provided for receiving and storing information read from the tag by the recipient to provide for further processing of the stored information including one or more of updating inventory, ordering refills, verifying patient vaccine schedules, and checking recalls. Similarly, a central repository may be provided for receiving and storing at least part of the information read from the tag to allow remote access or processing of the information including one or more of monitoring, agency compliance, and patient accessible records.

In further embodiments, the tag comprises wireless automatic identification technology comprising one or more of a passive device, a semi-passive device, an active device, a read only device, a read/write capable device, an optically readable device, a radio frequency identification (RFID) device, and a micro electromechanical system (MEMS) device. Moreover, the tag may include a MEMS-enabled tag wherein at least one sensor is a temperature sensor. The tag may inclde a bar code device combined with an RFID device.

In still further embodiments a reader is adapted to read the tag, where the reader is mounted in a location proximate a storage location for the product such that the reader may periodically read the tags automatically. A computer processor may be in communication with the reader and adapted to receive information from the reader and transmit information to the reader.

The method further includes populating a database, a file, a computer screen, a portable storage device, or other electronic record (e.g., EMR) with information read from the tag, updating inventories, ordering refills, checking with patient vaccine schedules, etc. The method further includes communicating some or all of said information to a central station/central computer/central database for monitoring and/or agency compliance and/or providing said information to the patient in electronic form.

Objects and advantages of the present invention include enabling remote office access to central database so that they can update their in-house database or update the central database; providing patient, physician, and pharmacist a standalone method of monitoring and maintaining vaccine or pharmaceutical data; eliminating barcode counterfeiting of vaccine and pharmaceuticals; monitoring vaccine and drug condition from origin to consumer and beyond; maintaining an electronic inventory; interacting with a variety of Electronic Medical Records (EMRs); providing emergency personal a quick and accurate way of accessing important patient information; eliminating the need for a separate database to decode vaccine and drug information (like with bar-coding); eliminating redundant entering and storage of medical information saving time for office personal; and helping to eliminate human error.

Micro electro mechanical systems (MEMS) have been used in several fields. Objects and advantages of MEMS devices for the present invention include the ability of those devices to carry out a number of functions and store large volumes of data compared with barcodes and the elimination of the inaccuracy inherent in barcode scanning and technology. MEMS provide a cost effective solution to individually track and monitor vaccines and pharmaceuticals throughout the supply chain and during storage and use. MEMS further ensure temperature/environment surveillance of vaccines and pharmaceuticals from origin to end user.

Further objects and advantages of the invention will become apparent from a consideration of the drawings and the technical description.

All patents, patent applications, provisional applications, and publications referred to or cited herein, or from which a claim for benefit of priority has been made, are incorporated herein by reference in their entirety to the extent they are not inconsistent with the explicit teachings of this specification.

BRIEF DESCRIPTION OF THE DRAWINGS

A more complete appreciation of the invention and many of the attendant advantages thereof will be readily obtained as the same become better understood by reference to the following detailed description when considered in light of the following drawings, wherein.

Figure 1:
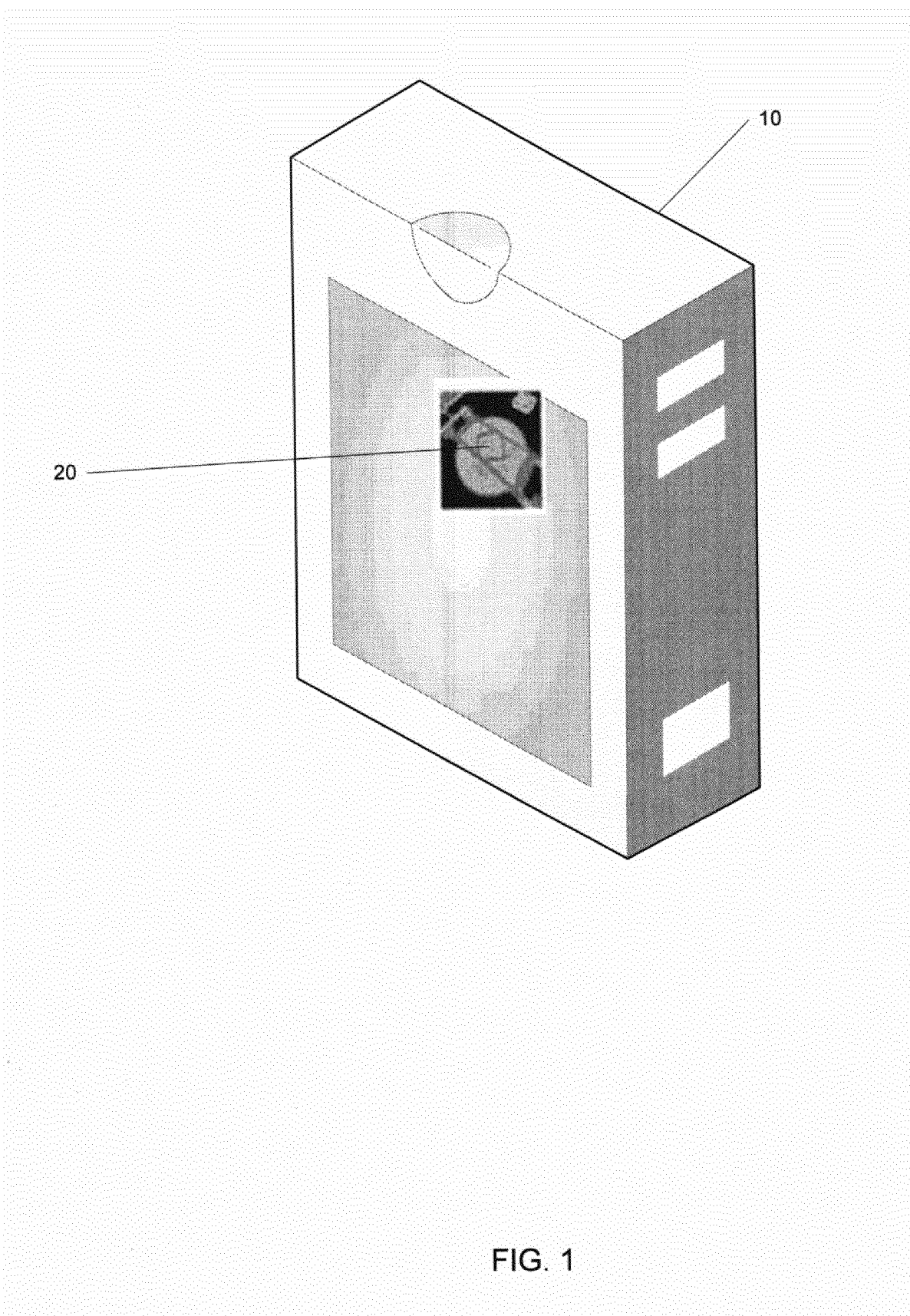
FIG. 1 shows a MEMS-enabled tag located on a vaccine or pharmaceutical product.

It should be understood that in certain situations for reasons of computational efficiency or ease of maintenance, the ordering of the blocks of the illustrated flow charts could be rearranged or moved inside or outside of the illustrated loops by one skilled in the art. While the present invention will be described with reference to the details of the embodiments of the invention shown in the drawing, these details are not intended to limit the scope of the invention.

DETAILED DESCRIPTION OF THE PREFERRED EMBODIMENTS

Referring now to the drawings, wherein like reference numeral designate identical or corresponding parts throughout the several views, embodiments of the invention are shown.

The present invention provides a system and method for tracking and monitoring vaccine and pharmaceutical information preferably using MEMS-enabled tags (e.g., a central unit that processes data, a microprocessor and several components that interact with the outside such as microsensors) to provide digital data storage on the tag, a communication interface (e.g., radio frequency (RF) transceiving and decoding electronics), and environment monitoring (e.g., temperature, radiation, humidity, time, etc). One aspect of the invention relates to a vaccine or drug product 10 that incorporates a MEMS-enabled tag 20 Tags are preferably placed on the individual vial/containers but may also be placed on the packages, cartons, transport vehicles, storage units, and the like. The MEMS-enabled tags are for use in identifying the vaccine or drug product as well as its environmental history. Another aspect of the invention relates to a system and method for reading the MEMS-enabled tags installed on vaccine or drug product 10 to obtain information. The system may link this information to a local computer/database or a remote/central computer/database for offsite monitoring. Another aspect of the invention relates to a method of tracking inventory in storage using the system. Each of these aspects will be discussed in greater detail below. Preferably, the MEMS technology is positioned on a tag 20 for ease in attachment to a package surface (e.g., vial or container) of the vaccine or drug product 10, or may be embedded in the packaging/container without a tag (collectively the MEMS technology of the present invention is referred to herein as a MEMS-enabled tag).

Micro Electronic Mechanical Systems (MEMS) devices are an integration of mechanical elements and electronics on a common substrate such as silicon. The electronics are fabricated using integrated circuit (IC) process sequences. The micro-mechanical components are fabricated using compatible "micro-machining" processes that selectively etch away parts of the substrate (e.g., silicon wafer) or add new structural layers to form the mechanical and electromechanical devices. MEMS sensing devices have low power consumption, are smaller, more functional, lighter, more reliable and are produced at a fraction of the cost of conventional macroscale devices.

Preferably, the MEMS-enabled tags are capable of providing data storage, wireless communications, sensing/actuation, and event capture where the event may be a temperature or moisture alarm, etc., and data transfer. MEMS-enabled tags may be powered utilizing local energy storage (e.g., battery, charged condenser, miniaturized fuel cells), energy harvesting, electromagnetic energy transmission such as used in RFID, and the like.

In certain embodiments, the MEMS-enabled tags comprise MEMS sensors coupled with radio frequency (RF) transceiving and decoding electronics for wireless communications and can thus detect and transmit parameters and/or environmental characteristic data for monitoring the vaccine and/or pharmaceutical during its service life (from origin to end user). RF tags, sometimes described as transponders, may be active (powered by a battery) or passive (acquiring energy from the incident radio frequency field). An RF reader is a device that is used to interrogate an RF tag for data. The reader has an antenna that emits radio waves; the tag responds by sending back its data.

The MEMS sensor and communication interface are preferably integrated into a single component (e.g., chip or substrate), or may alternatively be separate components operably coupled to each other. In an embodiment, an integrated, MEMS/RF sensor contains a data sensing component, a memory, and an RF antenna, whereby excitation energy is received and accesses one or more stored sensed conditions from memory and transmitting same via the RF antenna. The memory component may store raw and/or processed data received from the MEMS sensors, and the communications component may transmit raw data to the processor and/or transmit processed data to another receiver. The components (e.g., transceiver, processor, memory component, and communications component) are coupled together and in signal communication with each other.

Preferably, the MEMS sensor is constantly (or substantially constantly or periodically or frequently) monitoring the environment. In such an embodiment, a suitable power source is used (such as a battery). In an alternate embodiment, in order to conserve energy until sensor data is needed (i.e., when the sensor only periodically senses the environment rather than constant sensing), the MEMS sensor may be kept in a "sleep mode." (Or a combination of constant mode and optional sleep modes.)

When in sleep mode and not relying on a battery, when the sensors need to be activated, energy (e.g., RF or microwave) may be transmitted to the sensing device. The power and energy storage circuitry on the sensing device detects and rectifies the energy thereby powering the device. In such an embodiment, the method may include predetermined times in which the sensors are activated, such "X" times per days, or each time the environment significantly changes (e.g., moving the product to a different storage location). One embodiment may include continuous sensing during shipment and the option of sleep mode for extended storage once the product reaches the storage facility. Another embodiment may include continuous sensing and passive wireless communication wherein the MEMS sensor is constantly powered but the wireless communication relies upon excitation energy.

RF communication electronics used by the system may utilize passive, semi-passive, or active transponders. Each type of transponder may be read only or read/write capable. Passive transponders obtain operating power from the radio frequency signal of the reader that interrogates the transponder. Semi-passive and active transponders are powered by a battery, which generally results in a greater read range. Semi-passive transponders may operate on a timer and periodically transmit information to the reader. Active transponders can control their output, which allows them to activate or deactivate apparatus remotely. Active transponders can also initiate communication, whereas passive and semi-passive transponders are activated only when they are read by another device first. Multiple transponders may be located in a radio frequency field and read individually or simultaneously.

In operation, a reader communicates with the MEMS-enabled tag in a conventional manner. For example, with passive communication electronics, the reader powers the device so that the device communicates information stored thereon to the reader. The reader then communicates the information stored to a device such as a computer. In certain embodiments, the device may be written to by the reader to store additional information thereon. The information may either be written over existing information (if replacing information), or added to existing information. Information is also updated in the computer whenever inventory is moved or removed from storage. The reader may be activated automatically or manually. Readings performed by the readers may be continuous, intermittent, periodic, manual, as desired.

In the present embodiment discussed above, the communication electronics may be passive. However, a semi-passive or active system is also contemplated for use with the present design. If semi-passive or active communication electronics are utilized, a battery is coupled to the communication electronics. The MEMS sensor is electrically coupled to the communication electronics for communication. The sensor is used to read environmental or other conditions in the vicinity of the sensor. Examples of environmental properties include temperature and humidity, among other conditions. Multiple sensors may be utilized.

The MEMS sensors can transmit a sensed condition to be stored in memory or to the communication electronics when commanded to do so. In this regard, the communication electronics may be passive, semi-passive, or active. When the communication electronics are passive, the reader powers the communication electronics and the communication electronics then take a reading of the condition with the sensor. The sensed condition is then transmitted back to the reader. When the communication electronics are active or semi-passive, they are battery powered such that the communication electronics (and a clock) are continually powered. The battery powered communication electronics can independently signal the sensor periodically to sense a condition and the sensed condition is transmitted to storage in a log or immediate transmission to a reader. Certain types of sensors also require battery power and the power needed by the sensor may be provided by the same battery that is utilized to power the communication electronics.

In a preferred embodiment, as sown in FIG. 1, MEMS-enabled tags are attached to the containers/packaging of vaccines/drugs to aid in the combined functions of tracking and environment monitoring during handling, transportation and storage thereof. Information stored on the MEMS-enabled tag may include vaccine or drug specific data, for example, one or more of product name and type, lot number, expiration date, storage requirements (e.g., time/temperature), manufacturer, and the like. Environment monitoring of the MEMS-enabled tag may include, for example, temperature and/or humidity monitoring and/or a time function. Wireless communication of the MEMS-enabled tag may include, for example, RF (active or passive). Preferably, the MEMS-enabled tag provides one or more of the following functions: monitor temperature, radiation, humidity, time, etc., store digital data, communicate wirelessly to remote computer, survive and operate in diverse environments, allow re-programming (of certain data—for example, manufacturer data may be restricted).

Figure 2:
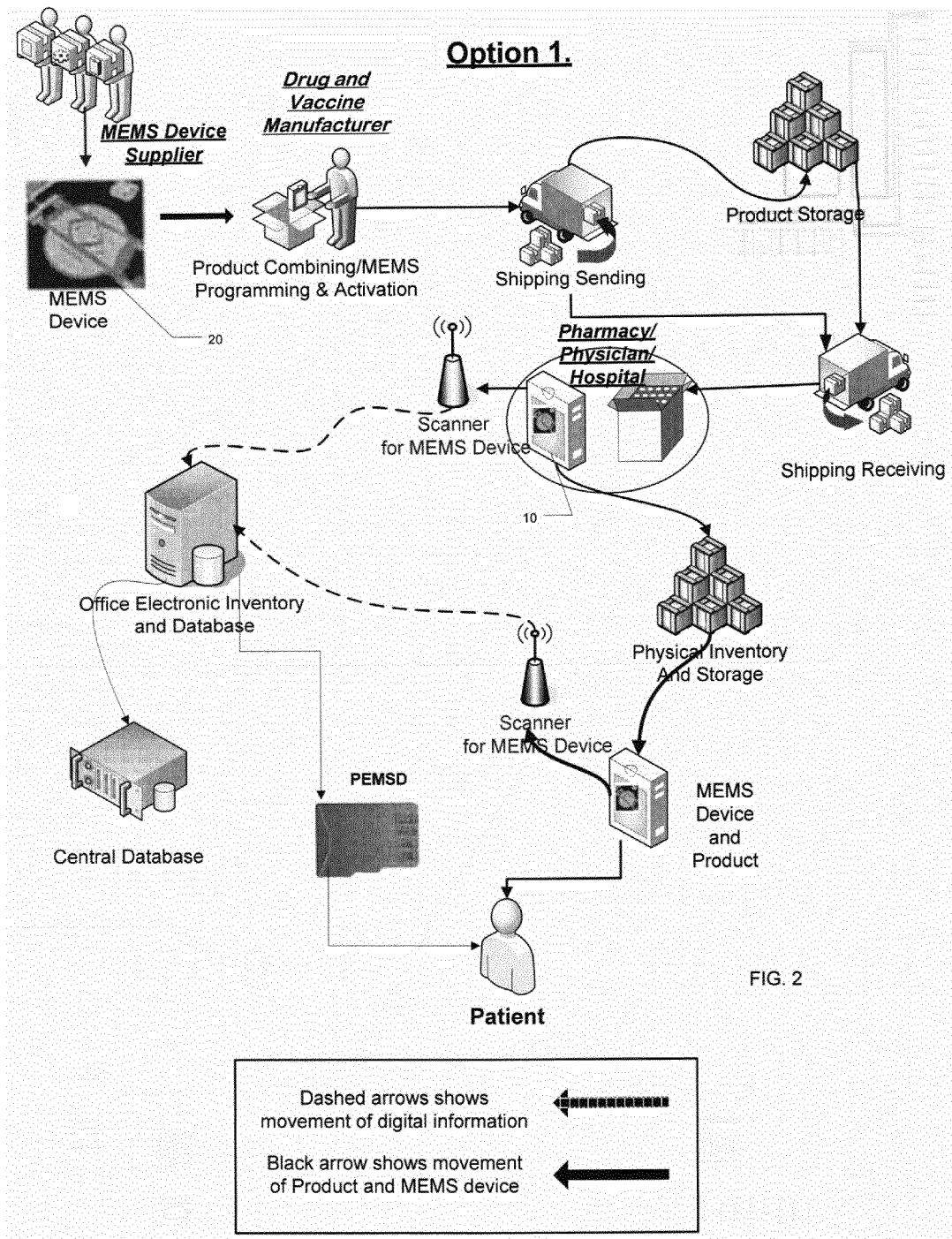
FIG. 2 illustrates a first embodiment of the invention for tracking and monitoring of the product during handling, storage, and use.

In a first embodiment of a method of the invention, as sown in FIG. 2, an un-programmed MEMS-enabled tag device (MEMSD) is delivered and programmed by the vaccine or pharmaceutical manufacturer. The MEMSD is programmed with vaccine or drug specific data to aid in tracking and monitoring of the product during handling, storage, and use. The MEMSD is incorporated into the current vaccine or pharmaceutical manufacturers automated packaging system. The MEMSD is attached to the container or vial in a non-removable and tamper-proof method. After packaging the MEMSD is activated and begins to monitor the product during shipping and storage on its way to pharmacies and or physician offices.

Upon arrival at a pharmacy and or physician's office the individual vaccine or pharmaceutical containers are checked for condition and accuracy by reading the MEMSD. If determined to be satisfactory, the product is then included in the physical inventory and scanned into an electronic inventory (in-house and/or central database are updated). The vaccine or pharmaceuticals are placed in their appropriate storage location until they are needed. While in storage the MEMSD continues to monitor the condition of the product (e.g., temperature, time, etc.). When the vaccine or pharmaceutical are needed they are pulled from storage and scanned to check for condition and included manufacturer data specific to the product. If the product is in good condition, the product in then administered to the patient through the appropriate method, and the container and attached MEMSD is properly disposed of. Each time the MEMSD is scanned, the in-house and/or central databases are updated. Scanning may occur for example upon receipt of the product, periodically during storage, after certain events (e.g., recent power outages which may have adversely affected the environment), before and after administering to a patient.

Figure 3:
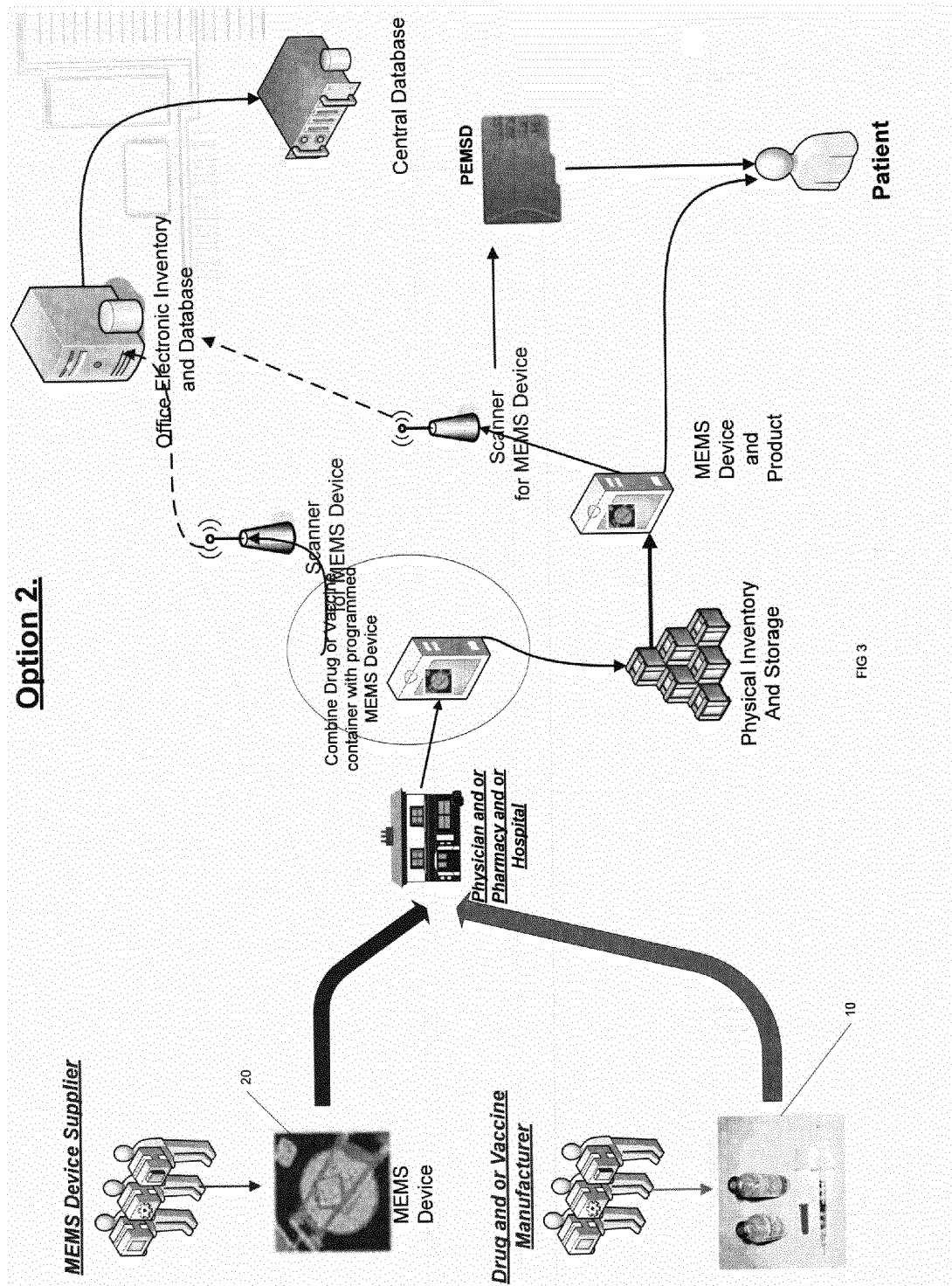
FIG. 3 illustrates a second embodiment of the invention for tracking and monitoring of the product during handling, storage, and use.

In a second embodiment of a method of the invention, as sown in FIG. 3, an un-programmed MEMSD is delivered and programmed by the pharmacies or physician, rather than at the manufacturer. The MEMSD is programmed with vaccine or drug specific data (supplied by the vaccine or pharmaceutical manufacturer) to aid in tracking and monitoring of the product during storage, and use. The MEMSD is attached to its appropriate vaccine or pharmaceutical container or vial, scanned, activated, and added to the physical and electronic inventory in its appropriate location. While in storage, the MEMSD continues to monitor the condition of the product (e.g., temperature, time, etc.). When the vaccine or pharmaceutical are needed they are removed from inventory and scanned to check for condition and included manufacturer data specific to the product scanned. The product is administered to the patient through the appropriate method, and the container and attached MEMSD is properly disposed of. Each time the MEMSD is scanned, the in-house and/or central databases are updated. Scanning may occur for example upon receipt of the product, periodically during storage, after certain events (e.g., recent power outages which may have adversely affected the environment), before and after administering to a patient.

Figure 4:
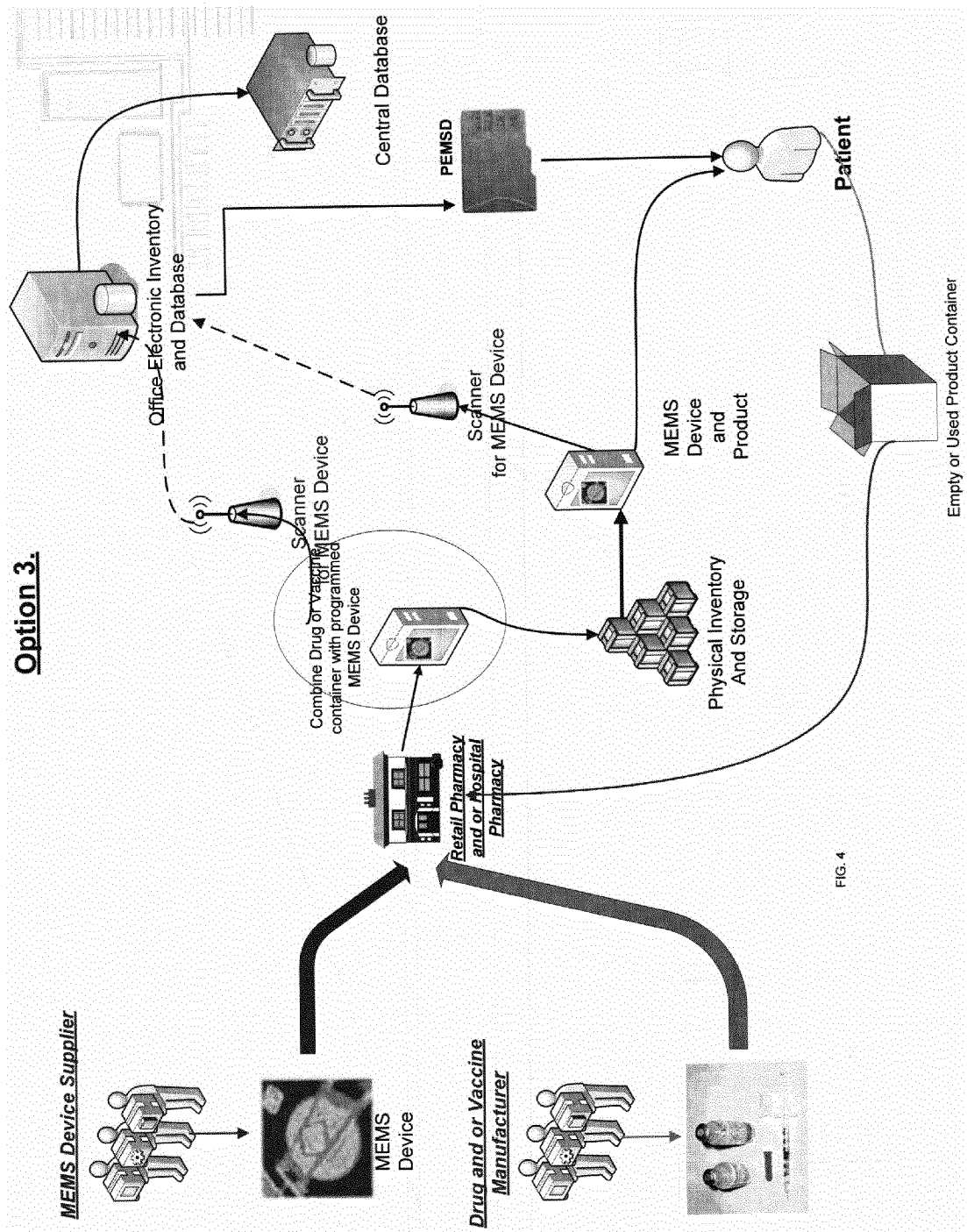
FIG. 4 illustrates a third embodiment of the invention for tracking and monitoring of the product during handling, storage, and use.

In a third embodiment of a method of the invention, as sown in FIG. 4, the method follows the same format as described above but allows for additional monitoring of pharmaceuticals once they are in a patient's possession. The supplying pharmacist can program a MEMSD with specific manufacture data, attach and activate the MEMSD. The MEMSD is packaged in a tamper proof manner with the patient's drugs so that prescribed pharmaceutical condition can be monitored. A patient can then scan the MEMSD at any time and check the condition or look at information included with the MEMSD. The patient can bring the container to the pharmacy to be refilled once empty where it can be scanned and checked for condition and accuracy when compared to the physician's prescription. The MEMSD can continue to be recycled in this manner until it no longer functions or the container is disposed of.

The physician software preferably has the capability of scanning vaccines' MEMSD when they arrive at the office. It may further have the ability to program and activate MEMSD when they are placed on vaccine containers not already including a preprogrammed MEMSD. The software checks the MEMSD to insure that the vaccine is acceptable and has not been damaged (e.g., exceeded certain environmental conditions that were monitored by the device) during shipping and/or storage. The software will be able to enter the vaccine type and any included information into an electronic inventory, thereby eliminating the need for manual entry of data. This may include but is not limited to: NDC number, lot number, expiration date, manufacturer, name of the vaccine and its components, administration, drug warnings, vaccine current and past condition, and VIS date. When a vaccine is retrieved from inventory, the MEMSD is scanned and the software checks the condition of the vaccine and assures the software user that the vaccine is suitable for use. It also updates the electronic inventory to match the depleted physical inventory.

To be sure that the right vaccine is being administered at the proper time, the software may utilize a patient vaccine schedule. The schedule will be automatically displayed when the patient demographics are entered into (or retrieved from) the system. The schedule would preferably be a standard Advisory Committee on Immunization Practices (ACIP) approved vaccine schedule but would have the capability to be customized as the physician's discretion. Once the vaccine is scanned, the program would indicate which vaccine was being administered and the date of administering. The nurse/administrator of the vaccine would then review the information and any changes made. The system could be programmed to output an alarm if a vaccine did not meet the requirements of the schedule. The nurse/administer would then indicate that the information was correct. Once the information was validated, the software would display specific Vaccine Information Sheets (VIS) for patient review, printing or downloading onto a Personal Electronic Medical Storage Device (PEMSD). A PEMSD is preferably a portable device that can store digital information such as a SD cards, Mini SD card, MP3 player, USB drive, smart card, or the like.

The Software stores the patient's demographic information, which includes primary and secondary insurance information, along with the current patient vaccine data (such as type of vaccine, route, site, expiration date, manufacturer, vaccine administrator, date of administration, VIS date, which stock inventory the vaccine was taken from, etc.) in an office database and sends the information to a secure central database which can be accessed, for example, only by authorized agencies. For example the local City/County Health Department could be one such agency. It will only send information specific to patient vaccine use. Also if any vaccines where recalled, the physician would enter the vaccine and Lot # into the software database search engine and the software would display all involved patient contact information. Or the software could automatically output an alarm related to such recalls.

The software will also have the capability to communicate and share data with a physician's current electrical medical record, eliminating the need to enter repetitive data into an office database.

The hospital pharmacist or retail pharmacist software preferably has the capability of scanning vaccines or other medications MEMSD when they arrive at the office. It may also have the ability to program and activate MEMSD when they are placed on product containers not already including a preprogrammed MEMSD. The software may check the MEMSD to insure that the pharmaceutical is acceptable and has not been damaged during shipping. The software may enter the pharmaceutical type and any included information into an electronic inventory. This may include but is not limited to: NDC number, lot number, expiration date, administration route, and drug warnings, current and past condition. When a drug is retrieved from inventory the MEMSD is scanned and the software checks the condition of the product and assures the software user that the medication is suitable to use. It also changes the electric inventory to match the depleted physical inventory.

The software may also be capable of downloading pharmacist and manufacturer information for the patient to access if needed on their PEMSD. In addition the software may be able to check the physician's prescription database for renewal and proper patient compliance.

The software may also send current patient prescription data to a secure central database. For example the local City/County Health Department could be one such agency. For example, it may only send information specific to patient pharmaceutical use.

The software may also have the capability to communicate and share data with a physician's current electrical medical record, eliminating the need to enter repetitive data into an office database The offices employing the invention software may utilize their own computer for an in-house database of patients treated. This will enable the system to be stand-alone. The software included in the system may further have the capability to send information to a central database. The central database could be maintained and monitored by an authorized agency. For example the local City/County health Department could monitor and maintain the central database. In addition to maintaining and monitoring the database, the governing agency could develop a nationwide network that could share the information with any medical office. Any medical office utilizing the invention software would be able to find current patient drug and vaccine records contained in the central database and be able to update their office database. Access will preferably be limited to only licensed and authorized administrators who have access to the invention software. Once approved demographic information along with vaccine and drug history will be sent or received from the central database.

Central Database Information preferably would include: Demographics (Date of Birth/Age, Address/Phone, Sex, Race, Primary and Secondary Insurance Information), Vaccine and Pharmaceutical (Vaccine or Pharmaceutical name, Manufacturer, Lot #, NDC #, Expiration date, Date of administration, Route of Injection, Site of Injection).

The patient software preferably will be able to take information downloaded from the physician and or pharmacy software stored on a PEMSD and display it on the patient's personal computer for viewing. The software may update the patient's stored records if new information is available on the PEMSD. This may include for example: name of drug, prescription directions, side effects and warnings, drug interactions, vaccine information sheets, vaccine information/potential side effects, and pharmacist and or physician comments and instructions. The software may have the capability for patients to manage their medical information through premade templates. Patients can enter in vaccine and drug history, billing information, insurance, or any other type of medical information that they wish. If a template does not exist matching the information that the patient wants to include, then the software may have the option of saving scanned documents and files as PDFs or the like. The patient software may also be able to download selected templates onto the PEMSD so that the information can be easily transported and shared if the patient wishes.

Each patient can be given a device (Personal Electronic Medical Storage Device (PEMSD)) that can store digital information. Examples might be: SD cards, Mini SD card, MP3 player, USB drive, SMART cards, or anything else capable of storing digital data. Medical information can be down loaded to the storage device through the physician's or pharmacist's or patient's software. The device can be programmed so that the vaccine or pharmaceutical records will automatically update (synchronize files) when connected to a computer containing the invention software. The patient can also have the option of downloading medical information of their choice to the storage device. This may include but is not limited to: demographic information, blood type, allergies, medical conditions, emergency contacts, physician and or pharmacist contact information, current and past prescriptions, and guardian contact information.

Security of the medical information is of great importance to protect the patient and their records. Information downloaded to the software can be in a read only PDF format with password protection, or the like. The password can be set by the patient at the time of enrollment in the database. Also to further enhance patient protection the PEMSD may utilize fingerprint protection by utilizing a built-in reader. Emergency response personnel can be given a version of the software that will override certain security features of the PEMSD. This can enable them a quick way to access patient medical data if the patient is not able to personally communicate the information or unable to remember clearly. The patient software can offer the user the option of allowing emergency personal access to selected templates that are downloaded to the PEMSD.

In an alternate embodiment, the invention may comprise barcode technology such as two dimensional or layered barcodes. These barcodes could be used alone or in conjunction with the Micro Electro Mechanical Systems (MEMS), Radio Frequency ID tags (RFID), or other technologies. The barcodes could contain the same product data such as: NDC number, vaccine or pharmaceutical name, manufacturer, lot number and expiration date. In the event that the MEMS device failed or was not present on the specific product upon arrival to its destination; the barcode could be scanned and product data recovered into the proposed patent software. The system may be linked with barcodes provided by the manufacturer and placed on the product at the time of creation. Barcode technology could provide a bridge to more advanced systems, and provide an incentive for regulatory agencies and manufacturers to expedite their efforts. Barcode data may be input into a data system in the same way and serve in the inventory, administration, patient safety, and efficiency of flow and distribution of data.

Obviously, numerous modifications and variations of the present invention are possible in light of the above teachings. It should be understood that the features may be used singly or in any combination thereof. The invention is also by no means limited to the particular embodiments that have been discussed above, or to even the variations that have been discussed in connection with them. For example, the invention also embraces systems which do not have many of the components that have been discussed above and/or which have additional components. A variety of commercially available tags, MEMS, and radio frequency integrated circuits are contemplated for use with the claimed invention. The present invention is not limited to having the components of either the remote or the central systems being at the same or at separate locations. The invention also contemplates that the functions of the invention will be implemented by hardware, software, firmware or by a combination of these, all in accordance with techniques that are well known. In fact, the present invention is not limited to systems that track vaccines and pharmaceuticals, but is also well-suited to systems that track other types of products which require environmental sensing and data storage. It is therefore to be understood that within the scope of the appended claims, the invention may be practiced otherwise as specifically described herein.

The invention claimed is:

1. A method for determining and tracking the safety and efficacy of a vaccine or pharmaceutical product having a tag with at least one environmental sensor and communications electronics associated therewith comprising:
   upon receipt of the product by a recipient associated with storing and administering or disbursing the product, determining the safety and efficacy of the product prior to adding the product to inventory by:
   (a) reading a tag associated with an individual vaccine or pharmaceutical product received, wherein the tag includes first information about the product, and wherein the tag further includes second information about the product recorded by an environmental sensor of the tag;
   (b) determining the safety and efficacy of the product based on the readings from the tag by:
      (i) comparing the first information read from the tag including an expiration date with a current date to determine whether the product has reached the expiration date indicating the product is expired;
      (ii) comparing the second information read from the tag including a range of environments read from the environmental sensor prior to receipt to a predetermined acceptable threshold range of environments for the product indicating whether the product has exceeded the threshold;
   (c) outputting information regarding the determination of safety and efficacy of the product, wherein if either determination indicates that the product is expired or the product has exceeded the environment threshold, designating that the product is unsafe and should not be administered; and
   upon retrieval of the product from inventory for administration to a patient, verifying the safety and efficacy of the product by repeating steps (a)-(c) and further verifying patient vaccine schedules, using a computer, prior to administration of the product by comparing a patient vaccine schedule for the product to the current date and the computer outputting an alarm should the comparison indicate an improper administration.

2. The method of claim 1 wherein the environmental sensor is activated when the product is packaged at the original place of packaging and wherein the environment sensor monitors one or more of temperature, humidity, moisture content, radiation, vibration, and light exposure.

3. The method of claim 1 wherein the first information about the product comprises product information for identifying the product and its place of manufacture capable of being used for inventory and tracking purposes.

4. The method of claim 1 further comprising repeating steps (a) though (c) at predetermined intervals, including one or more of (1) prior to administering the product, (2) after a designated time period has elapsed, (3) after a change in environment that may have an effect on temperature, (4) after moving the product to another location, (5) after a power interruption at a facility where the product is located, and (6) after receiving instructions from a third party.

5. The method of claim 1 further comprising sensors on the tag indicating elapsed time so that the expiration can be readily determined.

6. The method of claim 1 further comprising writing product information to the tag by the manufacturer, packager, or recipient.

7. The method of claim 1 further comprising populating a database with information read from the tag by the recipient to provide for further processing of the information including one or more of updating inventory, ordering refills, verifying patient vaccine schedules, and checking recalls.

8. The method of claim 1 further comprising communicating at least part of the information read from the tag to a central repository for remote access or processing of the information including one or more of monitoring, agency compliance, and patient accessible records.

9. The method of claim 1 wherein the tag comprises wireless automatic identification technology comprising one or more of a passive device, a semi-passive device, an active device, a read only device, a read/write capable device, an optically readable device, a radio frequency identification (RFID) device, and a micro electromechanical system (MEMS) device.

10. The method of claim 1 wherein the tag comprises a MEMS-enabled tag wherein at least one sensor is a temperature sensor.

11. The method of claim 1 wherein a reader adapted to read the tag is mounted in a location proximate a storage location for the product such that the reader may periodically read the tags automatically.

12. The method of claim 1 wherein a computer processor is in communication with the reader and is adapted to receive information from the reader and transmit information to the reader.

13. The method of claim 1 wherein the tag comprises a bar code device combined with an RFID device.

14. A system for determining and tracking the safety and efficacy of a vaccine or pharmaceutical product having a tag with at least one environmental sensor and communications electronics associated therewith comprising:
  at least one reader for reading the tag associated with the vaccine or pharmaceutical product;
  a computer processor in communication with the at least one reader for receiving information from the reader; the processor configured to
  upon receipt of the product by a recipient associated with storing and administering or disbursing the product, determine the safety and efficacy of the product prior to adding the product to inventory by:
    (a) reading a tag associated with an individual vaccine or pharmaceutical product received, wherein the tag includes first information about the product, and wherein the tag further includes second information about the product recorded by an environmental sensor of the tag;
    (b) determining the safety and efficacy of the product based on the readings from the tag by:
      (i) comparing the first information read from the tag including an expiration date with a current date to determine whether the product has reached the expiration date indicating the product is expired;
      (ii) comparing the second information read from the tag including a range of environments read from the environmental sensor prior to receipt to a predetermined acceptable threshold range of environments for the product indicating whether the product has exceeded the threshold;
    (c) outputting information regarding the determination of safety and efficacy of the product, wherein if either determination indicates that the product is expired or the product has exceeded the environment threshold, designating that the product is unsafe and should not be administered; and
  upon retrieval of the product from inventory for administration to a patient, verify the safety and efficacy of the product by repeating steps (a)-(c) and further verifying patient vaccine schedules, using a computer, prior to administration of the product by comparing a patient vaccine schedule for the product to the current date and the computer outputting an alarm should the comparison indicate an improper administration.

15. The system of claim 14 wherein the environmental sensor is activated when the product is packaged at the original place of packaging and wherein the environment sensor monitors one or more of temperature, humidity, moisture content, radiation, vibration, and light exposure.

16. The system of claim 14 wherein the first information about the product comprises product information for identifying the product and its place of manufacture capable of being used for inventory and tracking purposes.

17. The system of claim 14 wherein the processor is configured to repeat steps (a) though (c) at predetermined intervals, including one or more of (1) prior to administering the product, (2) after a designated time period has elapsed, (3) after a change in environment that may have an effect on temperature, (4) after moving the product to another location, (5) after a power interruption at a facility where the product is located, (6) after receiving instructions from a third party, (7) periodically throughout the day and record the temperature reading in a temperature log.

18. The system of claim 14 further comprising sensors on the tag indicating elapsed time so that the expiration can be readily determined.

19. The system of claim 14 wherein product information is written to the tag by the manufacturer, packager, or recipient.

20. The system of claim 14 further comprising a database for receiving and storing information read from the tag by the recipient to provide for further processing of the stored information including one or more of updating inventory, ordering refills, verifying patient vaccine schedules, and checking recalls.

21. The system of claim 14 further comprising a central repository for receiving and storing at least part of the information read from the tag to allow remote access or processing of the information including one or more of monitoring, agency compliance, and patient accessible records.

22. The system of claim 14 wherein the tag comprises wireless automatic identification technology comprising one or more of a passive device, a semi-passive device, an active device, a read only device, a read/write capable device, an optically readable device, a radio frequency identification (RFID) device, and a micro electromechanical system (MEMS) device.

23. The system of claim 14 wherein the tag comprises a MEMS-enabled tag wherein at least one sensor is a temperature sensor.

24. The system of claim 14 wherein a reader adapted to read the tag is mounted in a location proximate a storage location for the product such that the reader may periodically read the tags automatically.

25. The system of claim 14 wherein a computer processor is in communication with the reader and is adapted to receive information from the reader and transmit information to the reader.

26. The system of claim 14 wherein the tag comprises a bar code device combined with an RFID device.

* * * * *